United States Patent [19]

Bazin et al.

[11] Patent Number: 4,758,730
[45] Date of Patent: Jul. 19, 1988

[54] METHOD FOR EXAMINING THE SURFACE RELIEFS OF A SAMPLE AND APPARATUS FOR CARRYING OUT SAME

[75] Inventors: Roland Bazin, Vitry/Seine; Etienne Soudant, Antony; Patrick Trannois, Thomery, all of France

[73] Assignee: L'Oreal, Paris, France

[21] Appl. No.: 921,469

[22] Filed: Oct. 22, 1986

[30] Foreign Application Priority Data

Oct. 25, 1985 [FR] France ................... 85 15859

[51] Int. Cl.⁴ ............................................. G01N 21/86
[52] U.S. Cl. ..................................... 250/571; 356/376
[58] Field of Search ....................... 250/226, 571, 572; 356/237, 238, 371, 445–448, 376

[56] References Cited

U.S. PATENT DOCUMENTS

| | | | |
|---|---|---|---|
| 2,253,054 | 8/1941 | Tuttle et al. | 356/371 |
| 3,843,227 | 10/1974 | Kato et al. | 350/33 |
| 3,916,439 | 10/1975 | Lloyd et al. | 358/81 |
| 4,236,082 | 11/1980 | Butler | 250/461.1 |
| 4,349,277 | 9/1982 | Mundy et al. | 356/376 |

FOREIGN PATENT DOCUMENTS

| | | |
|---|---|---|
| 355629 | 8/1931 | United Kingdom . |
| 360782 | 11/1931 | United Kingdom . |
| 408899 | 4/1934 | United Kingdom . |
| 1244848 | 9/1971 | United Kingdom . |
| 2036362 | 6/1980 | United Kingdom . |
| 2041690 | 9/1980 | United Kingdom . |
| 2078944 | 1/1982 | United Kingdom . |
| 2148495 | 5/1985 | United Kingdom . |

*Primary Examiner*—David C. Nelms
*Assistant Examiner*—Stephone B. Allen
*Attorney, Agent, or Firm*—Cushman, Darby & Cushman

[57] ABSTRACT

The invention concerns a method for examining a sample whose surface comprises reliefs, and an apparatus for carrying out the method. The apparatus comprises a sample carrier plate subjected to illumination from at least two sources having different wavelengths and whose illumination axes form an acute angle of incidence on the sample carrier plate, the illumination axes of the sources being all different, and an observation system for the sample carried by the plate. The method may be used for measuring the effectiveness of a cosmetic treatment product on a skin.

17 Claims, 1 Drawing Sheet

METHOD FOR EXAMINING THE SURFACE RELIEFS OF A SAMPLE AND APPARATUS FOR CARRYING OUT SAME

FIELD OF THE INVENTION

The invention concerns a method for examining the surface of a sample and an apparatus for implementing this method. The method can, in particular, be used for examining the condition of skin, which is particularly important in the field of cosmetics where it is often necessary to study the action of a product on the skin, for instance the action of a product for attenuating wrinkles.

PRIOR ART

It is known that for examining the condition of a skin, it is common practice to take an impression of the skin zone concerned by means of a product forming a flexible film and giving a negative image of the zone to be investigated; in certain cases, a counter impression can then be made by means of a harder synthetic material which is moulded on the first impression and which thus restores the positive image of the zone to be investigated. This impression or counter-impression forms a sample which is deployed on an observation apparatus provided with a light source whose axis is oblique in relation to the median plane of the sample. This creates, on the side of each relief of the sample which is opposed to the light source, a cast shadow which shows the relief of the zone to be investigated in a clearly visible manner. The difficulty of such a method derives from the fact that nothing can be distinguished in the zone of the cast shadow so that the whole or part of each of the reliefs of the sample cannot become apparent with this type of sample. Moreover, if a relief has its median line substantially parallel to the axis of illumination, it does not create any cast shadow and therefore does not appear satisfactorily in the illuminated zone of the sample. If consideration is given to illuminating the sample with a second source identical with the first, but orientated along a different direction, the result is not satisfactory either, because although it is possible to distinguish what had previously been in the cast shadow zone, the relief effect is considerably reduced or even completely suppressed and the measurement of the height of the reliefs becomes impossible.

The assessment of the observation of a sample illuminated as indicated above can be effected either visually, for instance with a binocular microscope, or with an image analyser which defines in the field of observation the shadow zones and illuminated zones (in relation to an illumination threshold) on an all or nothing basis. For each shadow zone, a shadow surface is measured. The length of the said surface is measured substantially perpendicular to the illumination axis (termed "intercept"). From this one can deduce the mean width of the shadow zone; assuming the latter to be substantially rectangular and, knowing the inclination of the illumination axis to the median plane of the sample, the height of the corresponding relief is deduced therefrom. If the sample is the negative image of an area of skin, the height of the relief of the sample corresponds to the depth of a wrinkle.

OBJECT OF THE INVENTION

It is an object of the present invention to mitigate the drawbacks of the above-mentioned observation method and, in particular, to make it possible to observe the reliefs over the whole surface of the sample without thereby losing the relief impression.

It is also an object of the present invention to make it possible to observe the reliefs in the cast shadow zones and to take measurements relating to the height and length of these reliefs. In applying this method to cosmetics, the sample used may be either an area of skin of a living subject, or the image of such an area of skin obtained in the known way by taking an impression or a counter-impression. To measure the extent of the large or small wrinkles, it will generally be preferable to observe an impression providing a negative image of the skin zone investigated.

SUMMARY OF THE INVENTION

The invention consists in illuminating the sample under investigation with at least two sources emitting light of different colours, these sources having distinct illumination axes which are oblique to the median plane of the sample. In this way, each source provides a shadow zone which gives a relief effect, but the shadow zones relating to one of the sources are illuminated obliquely by the other light source or sources, so that the reliefs in the shadow zone remain visible to the eye and can be analysed, in particular by a colour analyser. The method in accordance with the invention thus makes it possible to obtain a complete view of the whole illuminated area of the sample without destroying the relief impression and this method makes it possible, if required, to take measurements of the reliefs over the whole illuminated zone, whereas previously the use of one single source, generally of white light, only allowed one observation over the illuminated zones since the shadow zones could only be reached by changing the position of the illumination axis in relation to the sample, which therefore necessitated a number of successive observations.

The present invention therefore provides a method for examining the surface of a sample, wherein the surface is illuminated by at least two light sources which emit light having different wavelengths, characterised by the fact that the sample is illuminated along an oblique direction in relation to the median plane of the observed zone of the sample to create cast shadow zones highlighting the reliefs, and in that the two light sources have different axes of illumination.

In a first variant, light sources are used having a narrow wavelength band distributed around a central wavelength, the central wavelengths of the different sources being different. These sources can be produced from a white light source by interposing a coloured screen. In a second variant, monochromatic light sources are used for instance by utilising low power lasers.

Advantageously light sources are used whose emission wavelengths correspond to primary colours, that is to say to red, to green or to blue; however it is also possible to use sources whose emission wavelengths correspond to complementary colours of a primary colour, that is to say, for example, to the yellow colour, (complementary of blue), to the colour of magenta, (complementary of green), or to the colour of cyan (complementary of red).

To light the sample, two or three light sources may be used. In particular it is advantageous to use three light sources providing, respectively, red, green and blue light beams. However, it is also possible to use two light sources, one of which emits light of a primary colour, whilst the other emits light corresponding to the complementary colour of that primary colour. To ensure good lighting of the sample it should be arranged that the illumination axes are angularly relatively distant from each other in relation to the sample; in particular it can be arranged that the illumination axes of two adjacent light sources form an angle of from 60° to 180°.

In order that the result obtained with the method in accordance with the invention may more readily be understood, the implementation of the method will be described below in the case where a green source and a red source are used which are disposed symmetrically in relation to the normal to the sample at its centre. In such a case, the green light will illuminate all the faces of the reliefs on the side of each relief nearer the green source, leaving the opposite faces of the said reliefs in shadow. On the other hand, the red light will illuminate the zones which were in the shadow of the green light. The zones illuminated by both light sources will appear as yellow because this colour results from a combination of red and green. If a long line relief is considered corresponding, on an impression, to a wrinkle of a skin specimen from which the impression was taken, the upper edge will appear as yellow and the two sides of the relief appear, one as green and the other as red. It can therefore be appreciated that the sample as a whole can thus be observed in one observation step. The result is improved still further if a blue light source is added to the device described above, for instance with its illumination axis in the plane of symmetry of the red and green light sources. In that case, in effect, all the reliefs having an orientation substantially parallel to the plane of the red and blue illumination axes will be highlighted by the shadows cast corresponding to the blue light. The image thus obtained can be analysed by a colour analyser which determines, at each point of the image the quantities of red, green and blue received by the said point, whence one may deduce the complete topography of the sample. It is clear that this topography will be the more accurate the narrower the band of the wavelengths emitted by each source and very good results are therefore obtained by using monochromatic lights.

The invention also provides an apparatus for carrying out the method defined above. This apparatus is characterised in that it comprises firstly a sample carrier plate subjected to the illumination of at least two sources with different wavelengths, whose illumination axes have an acute angle of incidence on the plate, the axes of illumination of the sources all being different, and secondly an observation system for the sample carried by the plate.

In a preferred embodiment the observation system cooperates with a photographic device or a colour analyser or a video system or an optical system for visual appraisal; the sample carrier plate may be capable of pivoting in relation to the light sources so that the best angle can be chosen for the sample in relation to the light sources, in particular in accordance with the reliefs in the sample.

BRIEF DESCRIPTION OF THE DRAWING

To render the invention more readily understood an embodiment thereof, represented in the attached drawings, will now be described by way of a purely illustrative and non-restrictive example.

In these drawings.

DESCRIPTION OF THE PREFERRED EMBODIMENT

Figure 1:
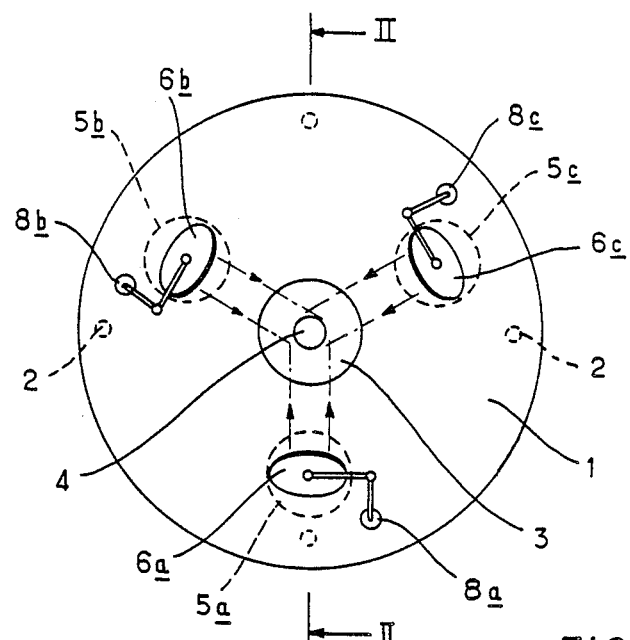
FIG. 1 represents an apparatus in accordance with the invention, viewed in plan.
Figure 2:
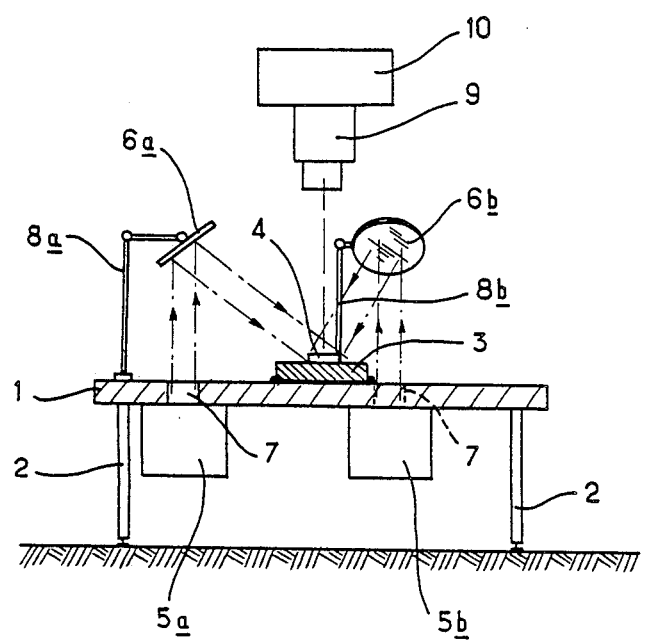
FIG. 2 represents a cross-section along II—II of FIG. 1, the observation system having been added directly above the sample.

Referring to the drawing, it will be seen that the apparatus is constituted by a base 1 supported by legs 2 on a supporting table. The base 1 is a circular disc comprising at its centre a circular sample carrier plate 3 on which the sample 4 to be observed is positioned. This sample 4 is an impression taken of an area of skin to be examined, the said impression forming a negative image of the skin area under investigation. The base 1 carries three light sources 5a, 5b, 5c each constituted by an incandescent lamp provided with a coloured filter; the sources 5a, 5b, 5c emit respectively in red, green, and blue. The plate 3 can rotate in relation to the base 1 so as to orientate the sample 4 to best advantage in relation the three light sources 5a, 5b, 5c. The three light sources, are fixed below the base 1 and the emitted beams are vertical. They pass through the base 1 via circular orifices 7, opposite which are mirrors 6a, 6b, 6c respectively. These three mirrors are supported by stands 8a, 8b, 8c respectively and their angle of inclination can be adjusted. The inclination of the three mirrors is adjusted in such a way that the beams emitted by the light sources converge on the sample 4. The position of the stands 8a, 8b, 8c is such that the axes of the three beams incidenton the sample are equiangularly distributed over one and the same cone having as its axis the normal to the sample at its centre.

Opposite the sample is an observation system 9, for instance, an optical system. The system 9 may be associated with a colour analyser 10, making it possible to measure the quantity of red, green and blue light at each point of the sample which is received by the said point. The angle of incidence on the sample 4 of the three cylindrical beams emanating from the three sources 5a, 5b, 5c is, for instance, 30°, that is to say that the beam axis forms an angle of 30° with the median plane of the sample.

The use of such a device makes it possible to cover all the reliefs of the sample in one single observation, irrespective of their orientation and to measure the heights and lengths of these reliefs by means of the colour analyser.

If one is content with a visual observation, replacing the colour analyser 10 by an optical device will allow a coloured image of the sample to appear; the coloration will vary along the zones and provide the observer with a perfect representation of the relief of the investigated zone, irrespective of the orientation of the relief portions projecting above the median plane.

The implementation of the method in accordance with the invention, and of the corresponding apparatus, is particularly useful in the field of cosmetics when it is desired to determine the effect a treatment product has on the skin, and in particular on the large and small wrinkles of an area of the skin.

It shall be duly understood that the embodiment described above is in no way restrictive and may give rise to any desirable modification without thereby departing from the scope of the invention as defined by the following claims.

We claim:

1. A method for investigating the surface of a sample in an observed zone having a median plane which zone of the sample may include reliefs comprising the steps of:
   illuminating the surface of said sample by means of at least two light sources which emit light having different wavelengths; and
   observing the illuminated sample;
   wherein the illumination of the surface of the sample is along a direction which is oblique in relation to the median plane of the observed zone of the sample to create cast shadow zones highlighting the reliefs, and the said at least two light sources having different axes of illumination.

2. A method according to claim 1, comprising the step of selecting said at least two light sources to have a narrow band of wavelengths distributed around a central wavelength, the central wavelengths of the different sources being different.

3. A method according to claim 1, comprising the step of choosing said light sources to emit monochromatic light.

4. A method according to claim 1, comprising the step of choosing two said light sources, one of which emits the light of a primary colour, whilst the other emits light corresponding to the complementary colour of said primary colour.

5. A method according to claim 1, comprising disposing the illumination axes of two adjacent said light sources so that they form an angle of from 60° to 180°.

6. A method according to claim 1, including the steps of obtaining an image of the illuminated sample and submitting said image to a colour analyser for determining the relief of the sample.

7. A method according to claim 1, comprising using an area of skin of a living subject as the illuminated sample.

8. A method according to claim 1, comprising using, as the illuminated sample, an impression obtained from an area of skin of a living subject.

9. A method according to claim 1, comprising the step of choosing said light sources to have emission wavelengths which correspond to the primary colours of red, green and blue.

10. A method according to claim 1, comprising the step of choosing said light sources to have emission wavelengths which correspond to the complementary colours of a primary colour.

11. A method according to claim 9, comprising using two said light sources.

12. A method according to claim 9, comprising using three said light sources.

13. A method according to claim 10, comprising using two said light sources.

14. A method according to claim 10, comprising using three said light sources.

15. Apparatus for carrying out a method for investigating the surface of a sample in an observed zone having a median plane where the sample may include reliefs in the observed zone and where the method includes the steps of illuminating the surface of the sample by means of at least two light sources which emit light having different wavelengths and observing the illuminated sample where the illumination of the surface of the sample is along a direction which is oblique in relation to the median plane of the observed zone of the sample to create cast shadow zones highlighting any reliefs with at the at least two light sources having different axes of illumination, comprising:
   (a) a sample carrier plate;
   (b) means for subjecting said sample carrier plate to illumination from at least two sources having different wavelengths and having illumination axes which form an acute angle of incidence on the sample carrier plate, the illumination axes of the sources being all different; and
   (c) an observation system for observing a sample carried by the sample carrier plate.

16. Apparatus according to claim 15, including one of photographic means, colour analyser means, a video means system, and an optical means for visual examination, said one means cooperating with said observation system.

17. Apparatus according to claim 15, including support means mounting said sample carrier plate for pivoting in relation to said light sources.

* * * * *